United States Patent

Larsson et al.

[11] Patent Number: 5,549,582
[45] Date of Patent: Aug. 27, 1996

[54] RESTRICTION DEVICE AND COUPLING FOR SELECTIVELY CONNECTING MULTIPLE CONDUITS MEETING AT A COMMON CONNECTION LOCATION

[75] Inventors: Rolf Larsson, Varby; Ulf Fahlstroem, Stockholm, both of Sweden

[73] Assignee: Siemans Elema AB, Solna, Sweden

[21] Appl. No.: 269,073

[22] Filed: Jun. 30, 1994

[30] Foreign Application Priority Data

Jul. 7, 1993 [SE] Sweden .................................. 9302356

[51] Int. Cl.$^6$ ............................................ A61M 25/00
[52] U.S. Cl. ........................ 604/283; 604/280; 604/3.84
[58] Field of Search ................................... 604/283, 103, 604/80, 86, 284, 905, 280; 137/247.19, 250, 625, 625.12, 625.15, 625.19, 625.21, 625.41, 625.46

[56] References Cited

U.S. PATENT DOCUMENTS

| | | |
|---|---|---|
| 3,517,669 | 3/1968 | Buono et al. . |
| 4,187,848 | 2/1980 | Taylor . |
| 4,758,235 | 7/1988 | Tu . |
| 4,850,980 | 7/1989 | Lentz et al. . |
| 5,084,031 | 1/1992 | Todd et al. . |
| 5,098,397 | 3/1992 | Svensson et al. . |
| 5,104,387 | 4/1992 | Pokorney et al. . |
| 5,348,542 | 9/1994 | Ellis ................................. 604/283 |

FOREIGN PATENT DOCUMENTS

WO92/21403  12/1992  WIPO .
WO93/00956  1/1993   WIPO .

*Primary Examiner*—Corrin M. McDermott
*Assistant Examiner*—N. Kent Gring
*Attorney, Agent, or Firm*—Hill, Steadman & Simpson

[57] ABSTRACT

A coupling for selectively connecting a plurality of conduits running to a common connection point, for controlling flows for medical purposes, includes a coupling element having one or more passages which, by rotation and/or displacement of the coupling element, are connectable to selected conduits for selective connection of the selected conduits at the same time as other conduits running to the connection point are closed by the coupling element so as to determine a flow path. The coupling element may be formed by a cannula, or alternatively may be formed by a coupling cone or element maneuverable by a cannula. In a restriction device for a conduit for carrying a fluid, especially for medical purposes, a first tube is connected to a channel extended through an elastic body. The body is surrounded by a stiff sleeve. A connecting second tube has a larger diameter than the diameter of the first tube and is intended for application against the elastic body from the side away from the first tube, a restriction thereby being obtained in the channel by axial compression of the elastic body by the second tube.

23 Claims, 9 Drawing Sheets

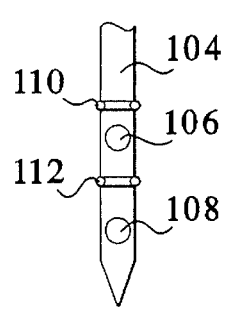
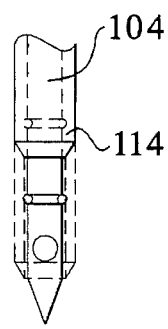
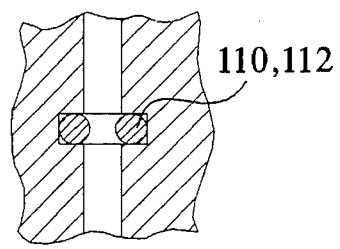
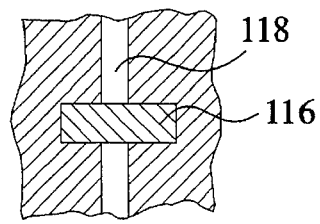
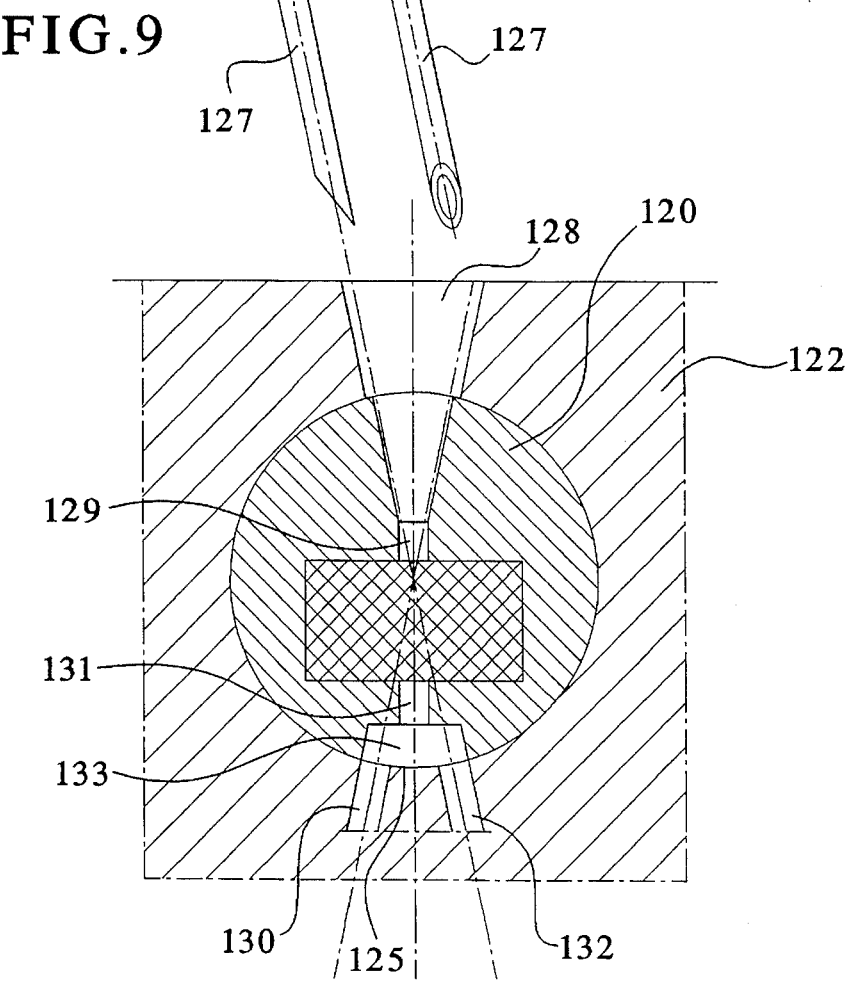

RESTRICTION DEVICE AND COUPLING FOR SELECTIVELY CONNECTING MULTIPLE CONDUITS MEETING AT A COMMON CONNECTION LOCATION

BACKGROUND OF THE INVENTION

1. Field of the Invention

The present invention relates to a coupling for selective connection of a plurality of conduits, running to a common connection point, to a restriction device for a conduit for carrying fluids, especially for medical purposes too.

2. Description of the Prior Art

In a number of application fields, there is a need for a multipath coupling between conduits running to a common connection point. The coupling must occupy very little space and have minimal dead volume. Such couplings are useful in, e.g., hydraulic systems, such as hydraulic control systems for space vehicles, spinal fluid drains, drug delivery (infusion) systems and in medical specimen-taking. A small dead volume means that the system in which the coupling is employed produces the least possible interference to fluid flow.

Currently, flushing of, e.g., catheters in implantable medication pumps can only be performed via the septum or directly through the catheter itself after the latter has been detached from the pump. The flushing of a limited part of a fluid tract is impossible, and the presence of dead volume causes an accumulation of air which can only be removed with great difficulty.

SUMMARY OF THE INVENTION

An object of the present invention is to provide a new simple type of multipath fluid coupling which is especially well suited for medical purposes.

The above object is achieved in accordance with the principles of the present invention in a coupling wherein a plurality of conduits are disposed in a connection piece so as to meet at common connection point, the connection piece having an opening therein. A coupling element is formed by a cannula having a longitudinal axis, the cannula being inserted into the opening and being maneuverable in said connection piece by either displacing the cannula along its longitudinal axis, or by rotating the cannula around its longitudinal axis. By maneuvering the cannula in this manner, a selected flow path is defined to at least one of the conduits, while simultaneously blocking a flow path to at least one of the other conduits. The cannula may have a passage therein terminating in an opening which, when the cannula is inserted into the connection piece, is positioned so as to be in fluid communication with one of the conduits. The (at least one) flow path which is defined by the cannula, therefore, may be a flow path from the cannula itself to the conduit, or may be a coupling of two or more conduits in the connection piece to each other. Alternatively, the coupling element may be formed by a movable element contained within the connection piece and disposed at the common connection point, which is maneuverable by the cannula.

With the present invention, a coupling is simply and cheaply achieved for selective connection of certain conduits at the same time as others are closed. A specific flow path is thereby achieved by the selection of a suitably devised coupling element.

With the coupling according to the invention, flushing of a desired part of a fluid tract is possible as well as emptying and filling of a flow system, such as an implantable medication pump.

The coupling according to the invention is not usable solely for achieving a desired pathway for the transport of a fluid but can also be used for controlling a wire, line or the like in a desired way, e.g., for cleaning purposes.

A limitless number of multipath connections can be provided with the invention.

In one embodiment of the coupling according to the invention, the coupling element includes means for fixing the element in one or more specific fixed positions. Thus, the end part of an injection cannula, for example, can be flattened to fit in a correspondingly shaped groove or slot in a fixing element on the other side of the connection point. In this way, the correct cannula position required for achieving the desired connection can be assured.

In another advantageous embodiment of the coupling according to the invention, the cannula has means for fixing its axial insertion position, and the cannula can have rotation and/or axial position markings to facilitate correct positioning of the element in the connection point.

In another advantageous embodiment of the coupling according to the invention, the cannula has a cylindrical body in which passages are devised on at least two axial levels, viewed along the cylinder body's longitudinal axis, for selective interconnection of conduits running to at least two interconnected connection points by rotation and/or axial displacement of the cylindrical body inside the conduit connecting the connection points. In such cases with conduits running to a plurality of connection points at different levels, the axial positioning of the cannula is therefore of decisive importance to correct attainment of the desired connection.

In other versions of the coupling according to the invention, the injection cannula is devised as an insertion tube, insertable into the connection point, with at least one opening in the tube wall, said opening being alignable with one of the conduits so this conduit communicates with the insertable tube at the same time as the wall of the insertable tube closes (blocks) the other conduits. The end of the insertion tube can be closed or open.

In the coupling according to the invention, the desired connections can be achieved not only by rotation and/or axial displacement of the coupling element, but also by translatory displacement perpendicularly to the conduits. According to yet another advantageous refinement of the coupling according to the invention, the coupling element has a displaceable slide for selective connection of the cannula to a plurality of conduits connected to the slide by displacement of the slide perpendicularly to the conduits. The slide can also be displaceable in perpendicular directions in an orthogonal plane relative to the connecting conduits. This embodiment permits a choice of a very large number of connectable conduits.

Another object of the present invention is to provide a new device for achieving a simple temporary or permanent restriction in a flow connection.

TAPE

The restriction device according to the invention can also be used for achieving increased pressure and sealing around e.g., a cannula inserted in the channel in the elastic body.

DESCRIPTION OF THE DRAWINGS

FIGS. 7a and 7b respectively show cannulae which can be used as coupling elements and which are supplied with ring seals for sealing against the conduit in which the cannula has been inserted in the cases in which the conduit's diameter is greater than the cannulas;

FIGS. 8a and 8b respectively shows one such ring seal in greater detail, and a septum seal.

FIGS. 9 and 10 show a fifth embodiment of the coupling according to the invention, in which the coupling element is devised as a rotating cone.

DESCRIPTION OF THE PREFERRED EMBODIMENTS

Figure 1:
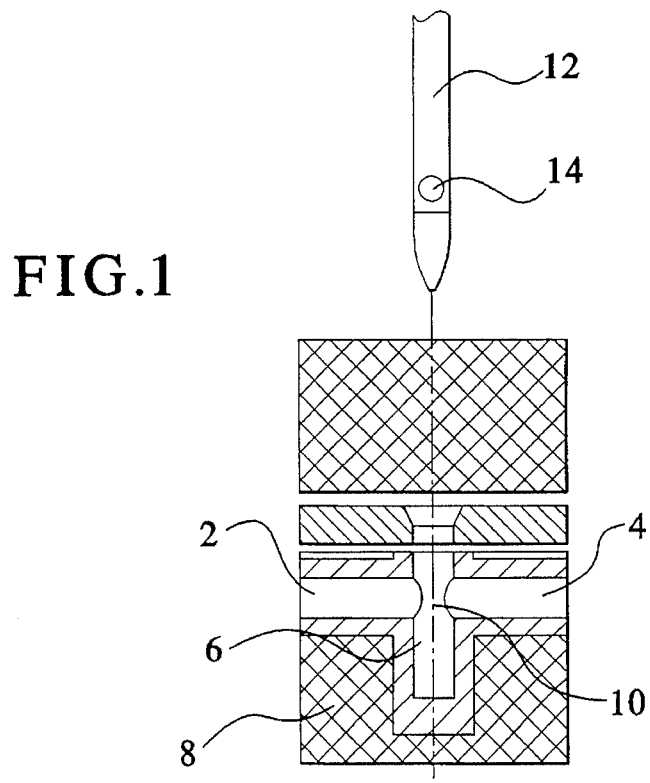
FIG. 1 shows a first embodiment of the coupling according to the invention.

In FIG. 1, two conduits 2 and 4 are shown running to a common connection point 10. A coupling element in the form of an insertable tube or cannula 12 is insertable through a hole 6 in a connection piece 8. An opening 14 in the wall of the cannula 12 is formed, which can be aligned with one of the conduits 2 or 4, after the cannula 12 has been introduced into the hole 6 so this conduit is connected to the interior of the cannula 12. The opposite conduit 4 or 2 is blocked by the wall of the cannula 12. When the cannula is rotated 180°, the cannula 12 can be connected to the other one of the conduits 4 and 2.

Figure 2A:
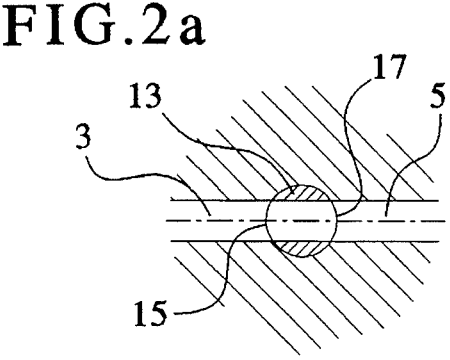
FIGS. 2a–2d respectively show different examples of multipath connectors which can be realized with the coupling according to the principle illustrated in FIG. 1.

FIG. 2a shows a two-way coupling in a cross section perpendicular to the section shown in FIG. 1, the coupling element being formed by a cannula 13 with two opposite openings 15 and 17 in the cannula wall. With the cannula 13 in the position shown in FIG. 2a, the conduits 3 and 5 are therefore connected to each other and to the interior of the cannula 13. When the cannula 13 is rotated, the interconnection of the conduits 3 and 5 is restricted, and the connection is completely blocked when the cannula 13 has been rotated 90°.

Figure 2B:
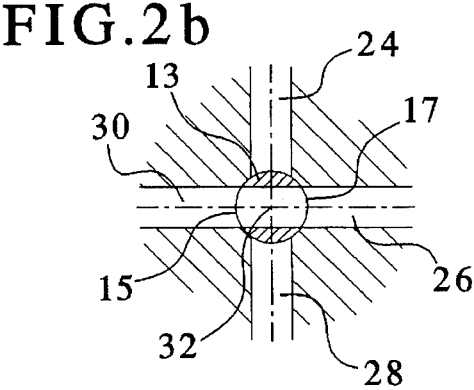

FIG. 2b shows a four-way coupling with a cannula 13 like the one shown in FIG. 2a as the coupling element. Four conduits 24, 26, 28 and 30 thus run in the same plane to a common connection point 32. With the cannula 13 in the position shown in FIG. 2b, the conduits 26 and 30 are interconnected, and the conduits 24 and 28 are connected to each other and to the interior of the cannula 13 when the cannula 13 is rotated 90°.

Figure 2C:
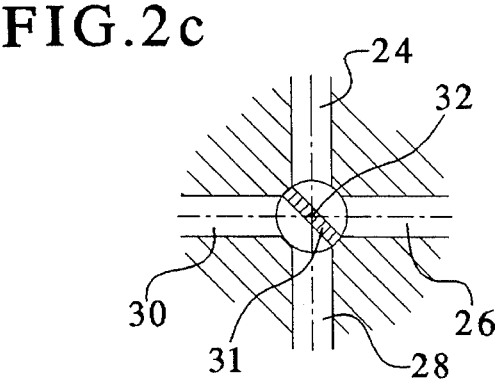

FIG. 2c shows a modified version of the four-way coupling in which the coupling element in the area of the common connection point 32 of the conduits 24, 26, 28 and 30 consists of a flattened and closed end part 31 of a cannula. With the cannula in the rotated position shown in FIG. 2c, the conduit 24 is connected to the conduit 26, and the conduit 28 is connected to the conduit 30. The conduits 24, 26, 28 and 30 are interconnected in different ways when the cannula is rotated.

Figure 2D:
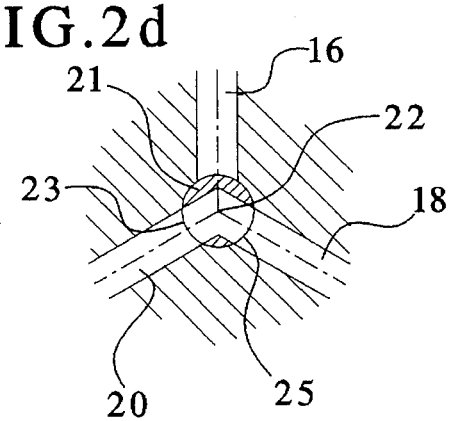

FIG. 2d shows a similar three-way coupling with three conduits 16, 18 and 20 running in a common plane to the connection point 22. The cannula 21 serving as a coupling element in this embodiment has two openings 23 and 25, displaced 120° in relation to one another, in the wall of the cannula to permit selective connection of the different conduits 16, 18 and 20 to each other and to the interior of the cannula when the cannula 21 is rotated.

Figure 3A:
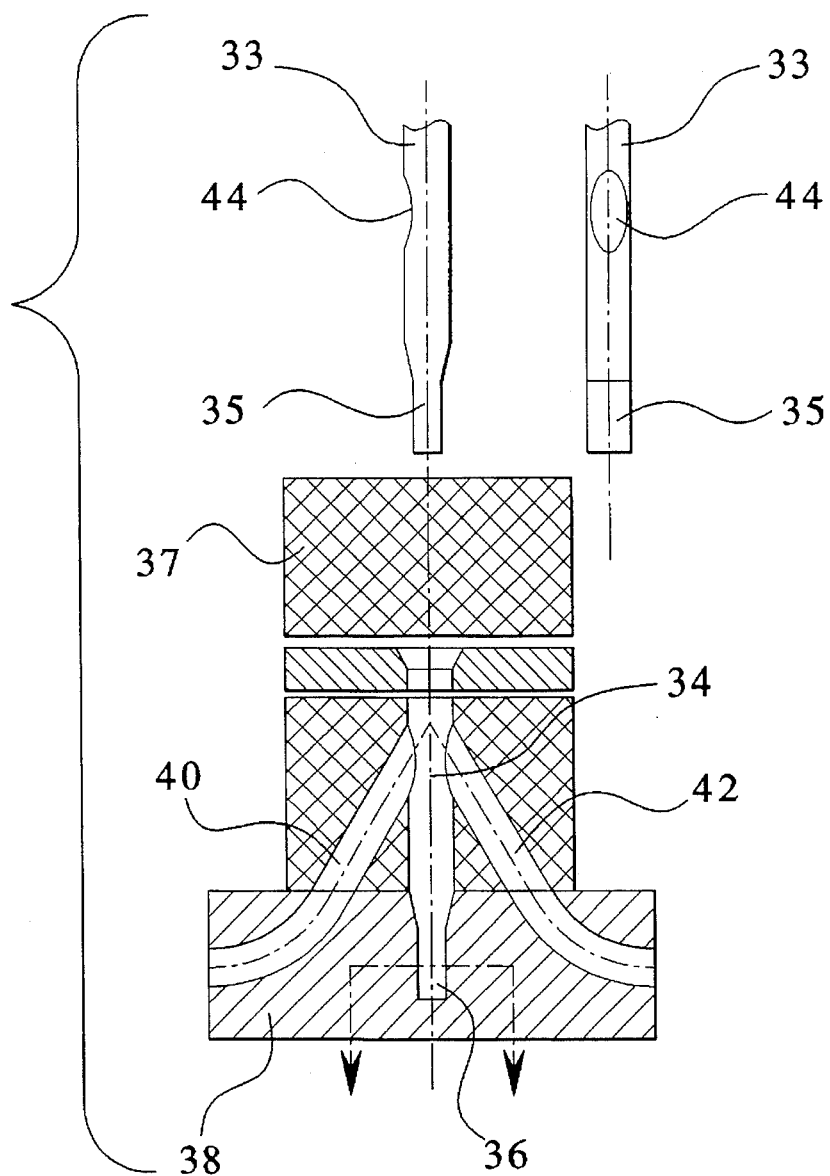
FIGS. 3a and 3b show a second embodiment of the coupling according to the invention in which the coupling element can be fixed in a given rotation position.

FIG. 3a shows an embodiment in which the coupling element is devised as a two-way or multipath tap which can be fixed in a defined rotation position. The coupling element 33 has a flattened end section 35, similar to the blade of a screwdriver, which is insertable into a corresponding slot 36 in a fixing piece 38 when the coupling element is inserted into the connection point 34. The coupling element 33 is hollow and has an opening 44 in its lateral wall in order to connect one of the two conduits 40 and 42 running to the connection point 34, to the interior of the coupling element 33. The correct axial position of the coupling element is assured when the end section 35 bottoms in the slot 36 in the piece 38.

Figure 3B:
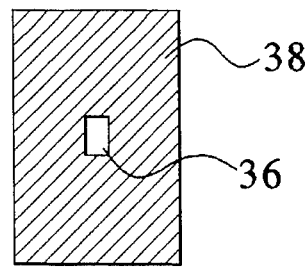

FIG. 3b shows a section, perpendicular to the cross-section shown in FIG. 3a, of a part of the fixing piece 38 with the slot 36. This Figure shows that the flattened end section 35 of the coupling element 33 is fixable in two rotation positions, displaced 180° in relation to one another in the slot 36, for connecting the interior of the coupling element 33 to each of the conduits 40 and 42.

The version shown in FIGS. 3a and 3b can clearly be devised as a multipath coupling with the coupling element fixable in a plurality of possible rotation positions.

A sealing septum 37 is pierced when the associated insertable tube or cannula is inserted into the connection point.

Figure 4:
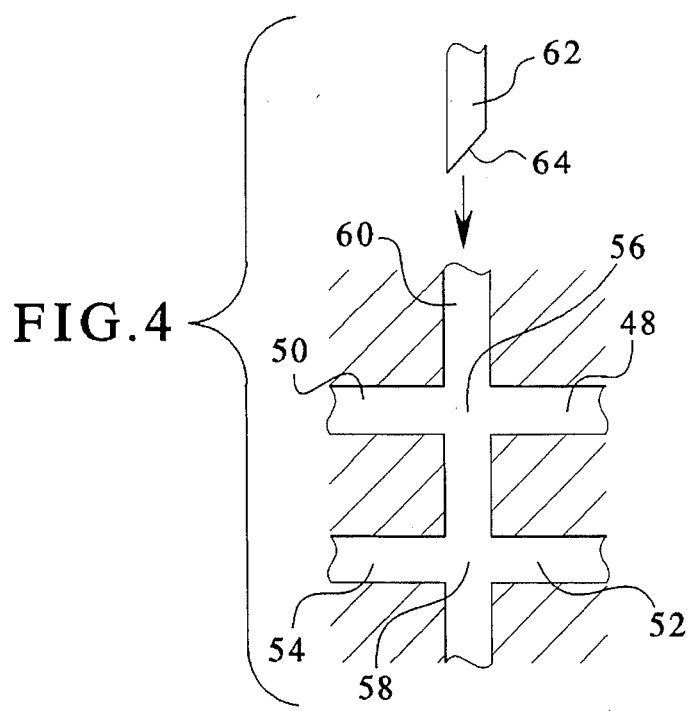
FIG. 4 shows a third embodiment of the coupling according to the invention, in which the conduits run to two connection points, located on two different levels.

FIG. 4 shows an embodiment in which the conduits 48 and 50 run to a connection point 56 and conduits 52 and 54 run to a connection point 58. The two connection points 56 and 58 are located on different levels along a conduit 60 connecting the connection points 56 and 58. The coupling element consists of an insertable tube or cannula 62. When the cannula 62 is axially displaced and rotated inside the conduit 60, the opening 64 of the cannula 62, and, accordingly, the interior of the cannula 62 and the conduit 60, can be connected to one of the conduits 48, 50, 52 and 54 in an optional manner at the same time as the cannula 62 block the other conduits. The cannula 62 can also be brought to a position in which it blocks all the conduits 48, 50, 52 and 54, and the coupling only maintains one axial connection through the cannula 62.

Figure 5A:
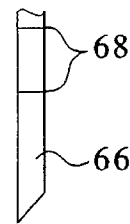
FIGS. 5a–5c respectively show three different examples of cannula which can be used as a coupling element in the embodiment illustrated in FIG. 4.

FIG. 5a shows a cannula 66 with level markings 68 for determining the axial insertion position of the cannula 66.

Figure 5B:
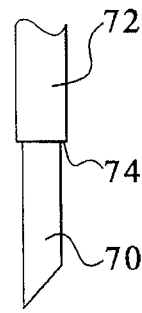

FIG. 5b shows a cannula with different diameters in different sections 70 and 72 so a shoulder 74 is formed between them. When this cannula is used in the coupling in FIG. 4, the cannula part 70 is insertable into the conduit 60 until the shoulder 74 is pressed against the rim of the conduit 60, thereby fixing the cannula's axial position. In that axial position, the cannula part 70 can block the conduits 48 and 50 while leaving the conduits 52 and 54 open.

Figure 5C:
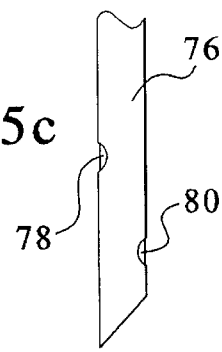

FIG. 5c shows a cannula 76 with two openings 78 and 80 in the cannula wall. When this cannula 76 is used in the coupling shown in FIG. 4, the conduit 50 can, e.g., be connected to the conduit 52 at the same time as the conduits 48 and 54 are blocked and by rotating the cannula 76 by 180° the conduits 48 and 50 are connected while simultaneously the conduits 50 and 52 are closed.

The cannula shown in FIG. 5c can easily be devised with a plurality of openings, located in different positions, to make possible a plurality of different versions of conduits interconnected by rotation and axial displacement of the cannula.

Figure 6:
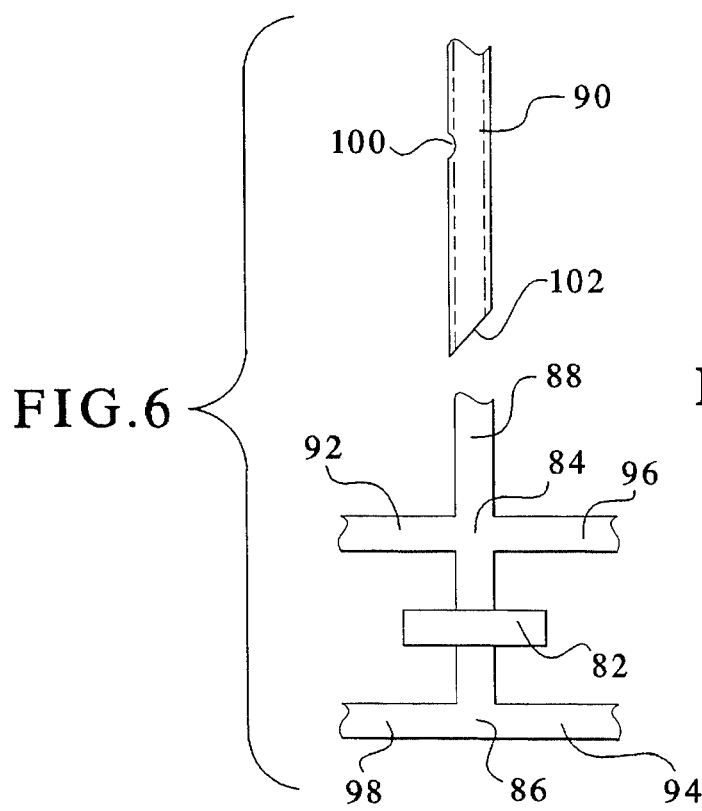
FIG. 6 shows a fourth embodiment of the coupling element according to the invention, the connection points shown in the embodiment illustrated in FIG. 4 being separated by a septum.

FIG. 6 shows a version of the coupling shown in FIG. 4 in which a septum 82 is arranged in the conduit 88 connecting the connection points 84 and 86. The septum 82 can be pierced by the cannula 90 which thereby connects, e.g. the conduits 92 and 94 through the openings 100 and 102 of the cannula 90 at the same time as the conduits 96 and 98 are blocked. By rotating the cannula 90 by 180°, the conduits 96 and 98 can be interconnected instead in this instance.

FIG. 7a shows a cannula 104 with openings 106 and 108 at different axial positions. The cannula 104 is intended for introduction into a conduit with a somewhat larger diameter and is therefore provided with ring seals 110 and 112 for sealing against the interior of the conduit.

FIG. 7b shows the cannula 104 of FIG. 7a provided with an external protective sleeve 114.

The cannula 104 can be of a double-lumen design so the openings 106 and 108 are respectively in connection with separate channels inside the cannula, these channels thus, according to the invention, being interconnectable via the cannula to different conduits.

The cannula 104 in FIG. 7a is equipped with ring seals, however, in instances in which the diameter of the conduit is greater than the diameter of the cannula, one or more ring seals 110 or 112 can be disposed in an annular recess surrounding the conduit, as shown in FIG. 8a. Alternatively, a septum seal 116 (of FIG. 8b) can be disposed in the conduit 118 used through which the insertable tube or cannula passes.

Figure 10:
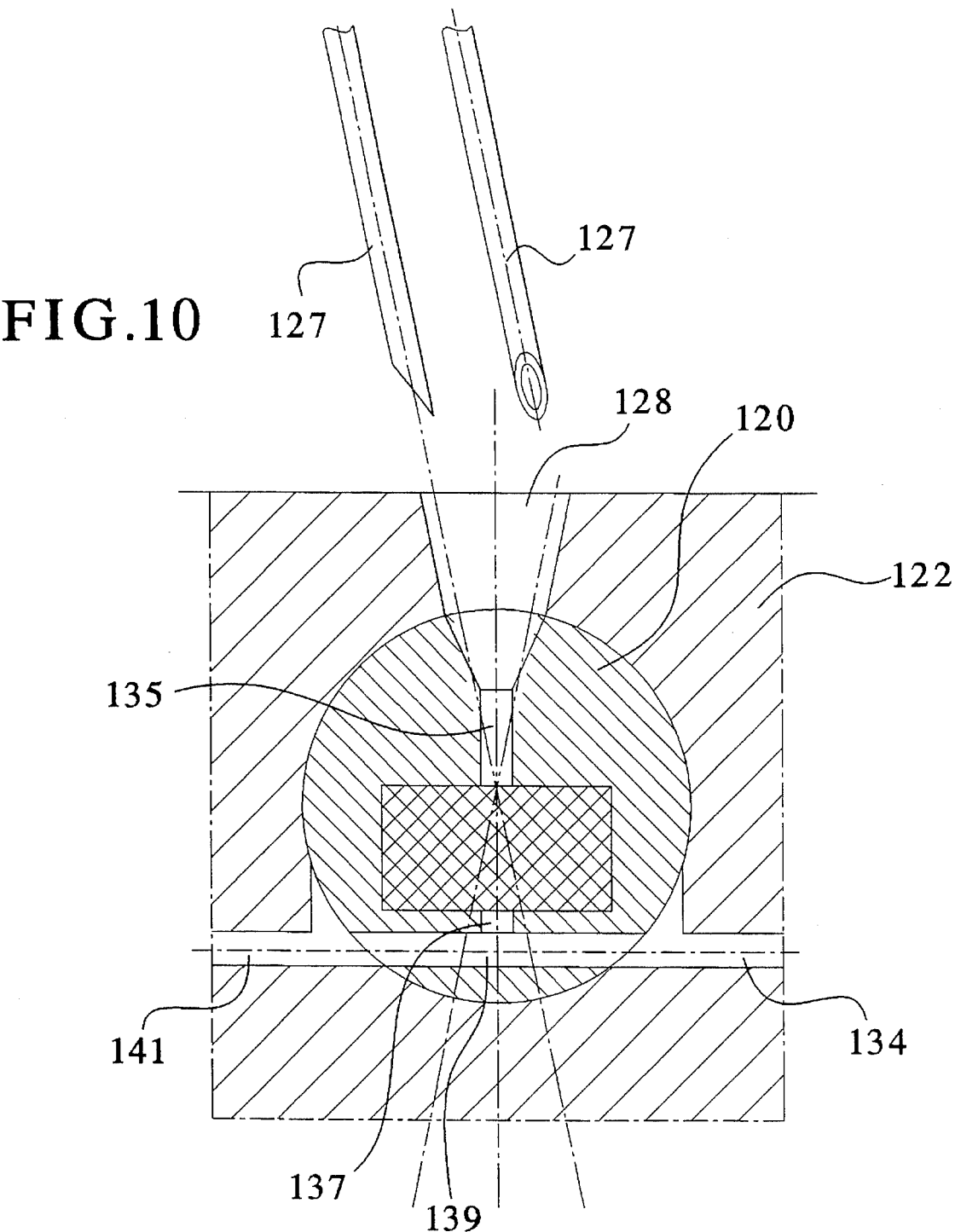

FIGS. 9 and 10 respectively show two embodiments in which the coupling element is devised as a rotating cylinder 120 in a connection piece 122. The cylinder 120 is maneuverable (rotatable) with a cannula 127 inserted into the channel 128 and is devised with one or more passages to make possible selective connection and closure of the channels 128, 130, 132, 134 and 141 in the connection piece 122 by rotation of the cylinder 120 in the connection piece 122. The cone 120 can be manipulated with a wire or some other suitable element in addition to the cannula 127.

In the position shown in FIG. 9, the channel 128, and the contiguous channels 129, 131 and 133 in the rotating cylinder 120, are connected to both the channels 130 and 132. When the cannula 127 is introduced into the channel 128 and further into the channel 129, the cylinder 120 can be rotated in either direction with the cannula 127 so the channels 129, 131 and 133 in the cylinder 120 are only connected to one of the channels 130 and 132.

If the cylinder 120 is not in such a rotational position in which the cannula 127 is aligned with one of the channels 130 or 132, the cannula 127 will bump into the material 125 in the connection piece 122 between these channels 130 and 132. Thus a stop is obtained which prevents additional insertion of the cannula 127 when it is not aligned with one of the channels 130 or 132.

In the embodiment of FIG. 10, the channel 128 in the illustrated position is connected, via contiguous channels 135, 137 and 139 in the cylinder 120 to the channels 134 and 141. When the cylinder 120 is rotated with the cannula 127 in the same way as in the embodiment shown in FIG. 9, the connection to either channel 134 or 141 can be blocked. When the cylinder is rotated clockwise, the connection to the channel 134 closes and when the cylinder 120 is turned counter-clockwise, the connection to the channel 141 closes.

Figure 11:
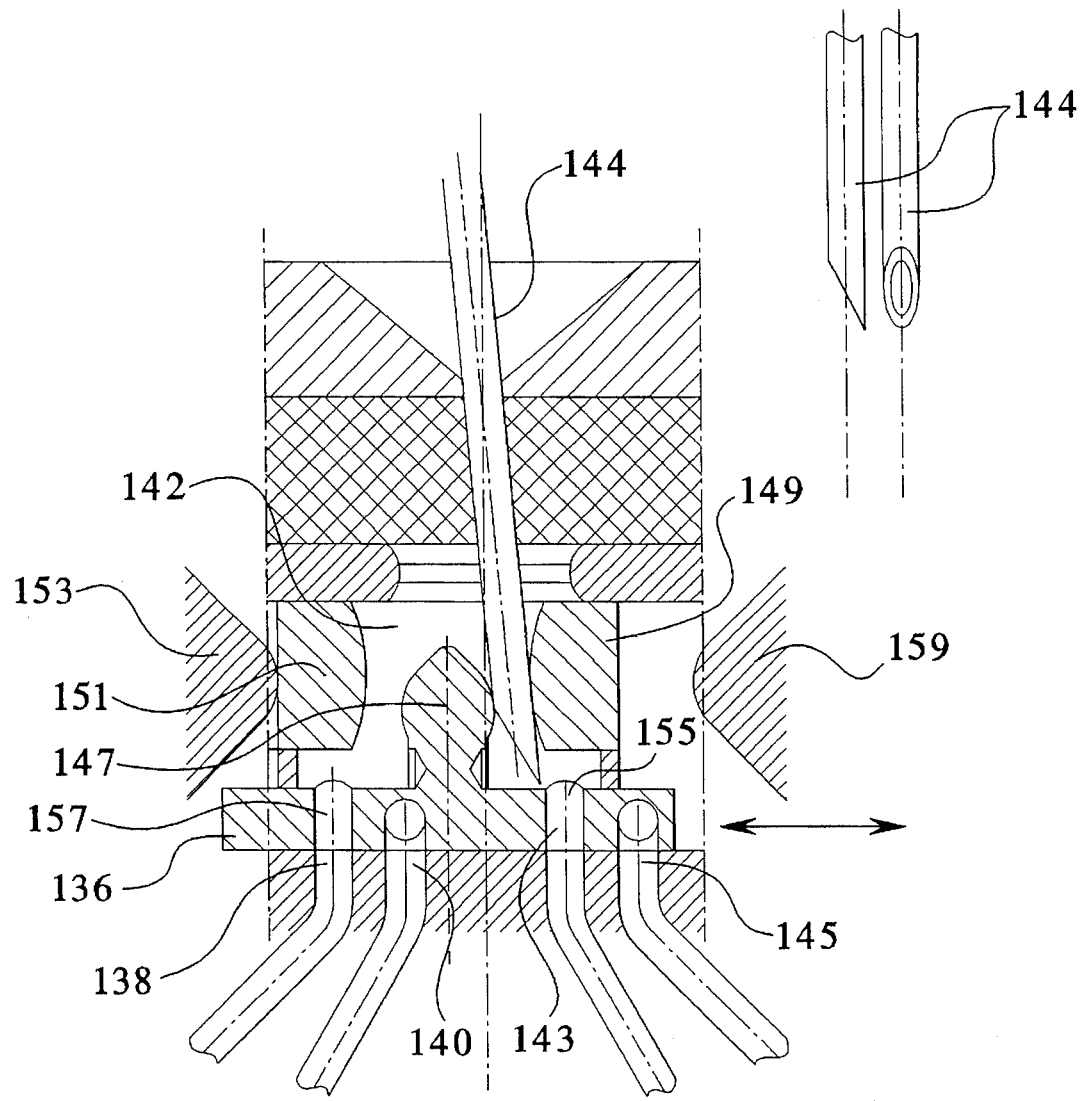
FIG. 11 shows a sixth embodiment of the coupling according to the invention, in which the coupling element is a displaceable slide.

FIG. 11 shows an embodiment in which the coupling element is devised as a slide 136 which can be displaced in a direction perpendicular to the conduits. In the lower side of the slide 136, there are four orifices 138, 140, 143 and 145 which open onto a space 142 inside the slide 136. FIG. 11 shows an insertable tube or a cannula 144 in fluid communication with a conduit, having the orifice 143 via the channel 155 in the slide 136.

In the position shown in FIG. 11, the cannula 144 has been inserted between sealing shoulders 147 and 149, and the slide 136 is in the left position in FIG. 11 with the left end shoulder 151 of the slide 136 bearing against the stop 153.

By displacing the slide 136 to the right against the right stop 159 the channel 155, and thus the cannula 144, is in fluid communication with a conduit having the orifice 145.

When the cannula 144 is inserted between the sealing shoulders 147 and 151, the cannula 144 can, in a similar manner, be placed in fluid communication, via the channel 157 in the slide 136, with one of the conduits having the orifices 138 and 140 in an optional manner by displacing the slide 136.

In the embodiment according to FIG. 11, the slide 136 can be devised to be displaceable also perpendicular to the plane of the drawing in order to increase the number of conduits which can be connected to the cannula. The coupling can further be devised so a larger number of conduits, for every cannula position, is selectively connectable by successive movement of the slide between the end positions. This version of the coupling makes it possible to select a very large number of connectable conduits.

Figure 12:
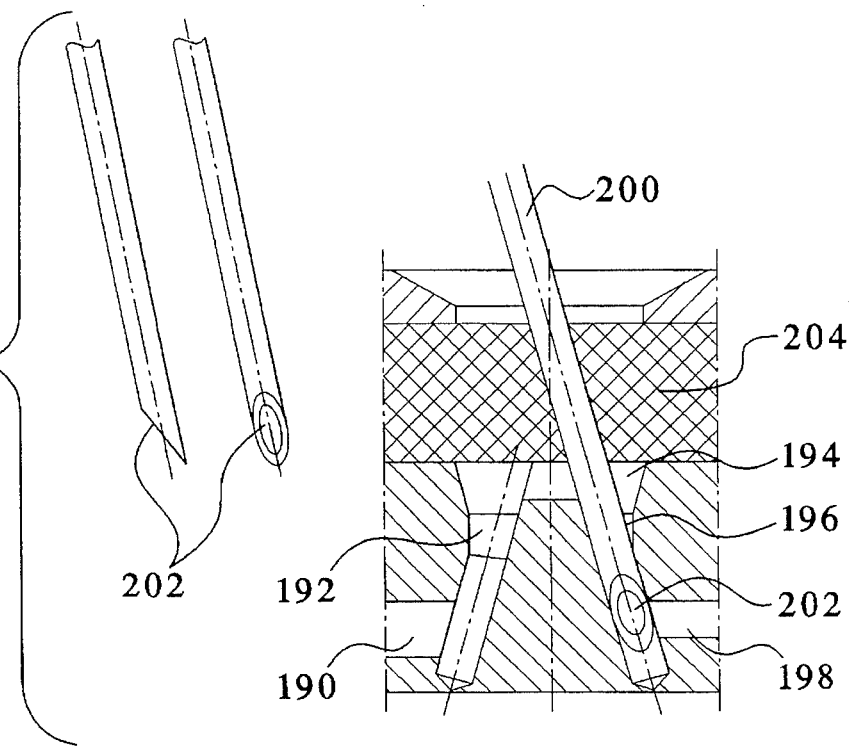
FIG. 12 shows a seventh embodiment of the coupling according to the invention, in which the coupling element again consists of a cannula.

FIG. 12 illustrates an embodiment in which two conduits are interconnectable via the channel system 190, 192, 194, 196 and 198. By inserting a cannula 200 through a sealing septum 204 into the contiguous channel 194 and 196 with the cannula orifice 202 in connection with the channel 198, the interior of the cannula 200 is in fluid communication with a conduit (not shown) connected to the channel 198. The cannula 200 is devised to seal against the interior of the channel 196. The connection to the channels 192 and 190 is therefore blocked. When the cannula 200 is introduced in the corresponding way into the channel 192, the interior of the cannula 200 is in fluid communication with a conduit (not shown) connected to the channel 190.

Figure 13A:
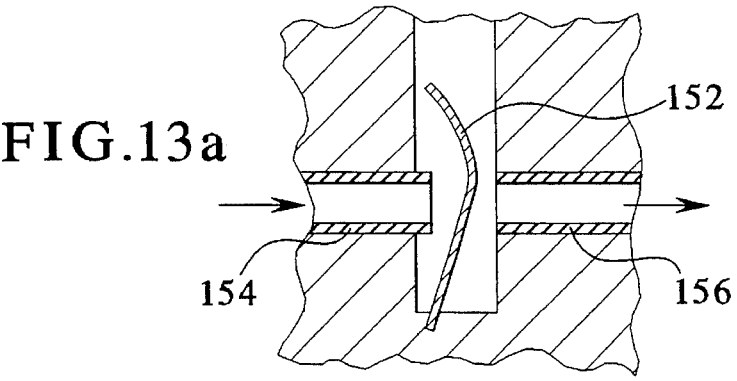
FIGS. 13a and 13b show an eighth embodiment of the coupling according to the invention, in which the coupling element is a flexible tongue element.
Figure 13B:
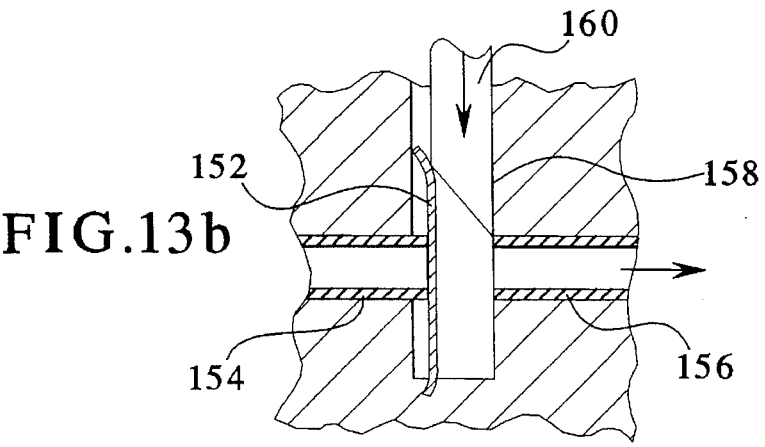

FIGS. 13a and 13b shows an embodiment in which a tongue element 152 is arranged in the connection point. The element 152 is spring-biased and is curved such that the orifices of both conduits 154 and 156 are exposed when the cone is untouched. The conduits 154 and 156 in FIG. 13a are thus interconnected.

FIG. 13b shows how the element 152 is acted upon by a cannula 160 inserted into the conduit 158 so the conduit 154 is closed. In this case, the interior of the cannula 160 is connected to the conduit 156.

In addition to the mechanical action on the element 152 shown in FIG. 13b, the element 152 can be actuated by a fluid flowing through the conduit 158 to press against the orifice of the conduit 154.

Figure 14A:
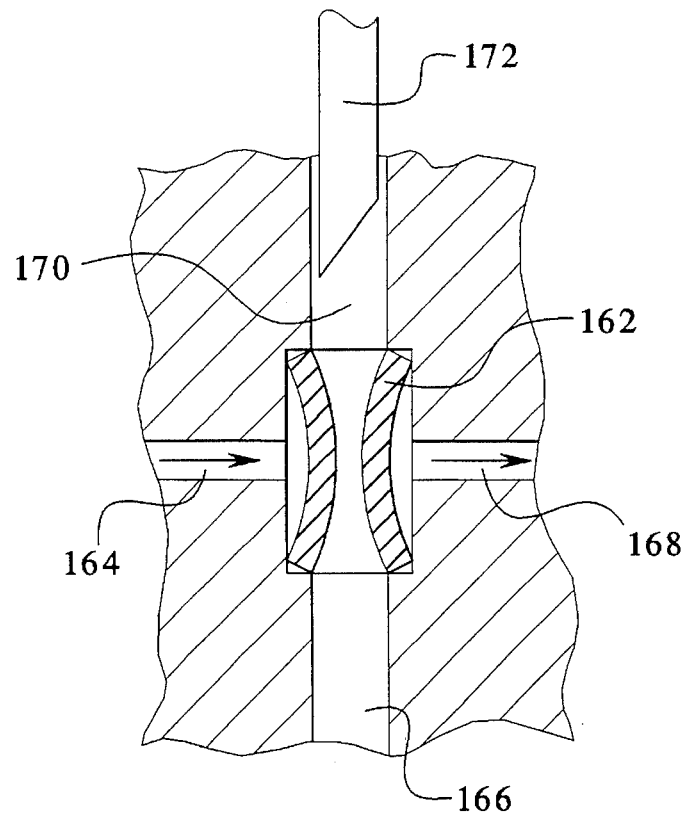
FIGS. 14a and 14b show a ninth embodiment of the coupling according to the invention, in which the coupling element is a cylindrical sealing element.
Figure 14B:
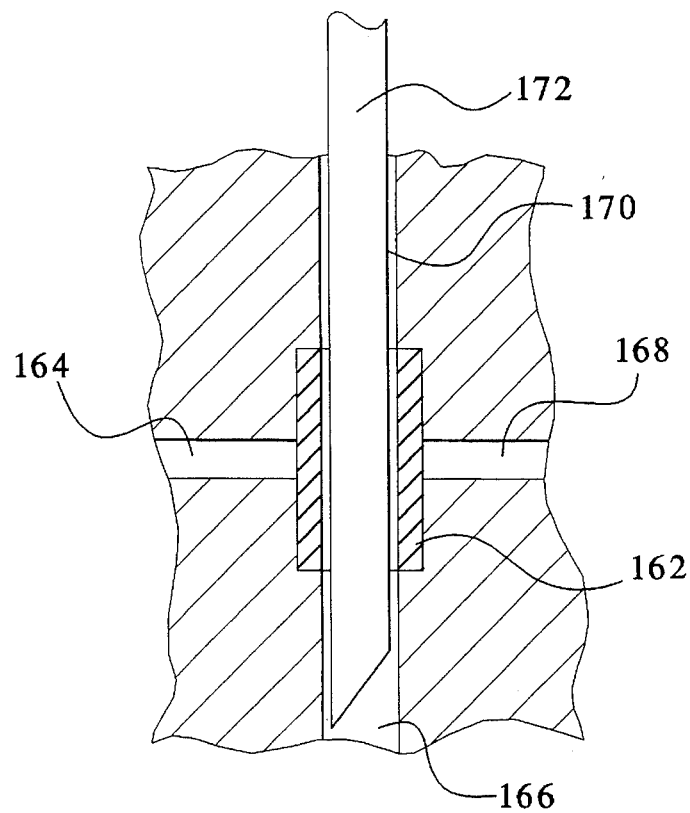

FIGS. 14a and 14b shows an embodiment in which a cylindrical sealing element 162 is arranged in a specially adapted space in the connection point for the conduits 164, 166, 168 and 170. The sealing element 162 consists of an elastic material and is devised to curve inwardly so the orifices of the conduits 164 and 168 are unobstructed (see FIG. 14a, which shows the sealing element 162 in the unaffected state). In this position, therefore, there is a connection between the conduits 164 and 168.

In FIG. 14b, the cylindrical element 162 is acted on by an insertable tube or a cannula 172 and is pressed against the orifice of the conduits 164 and 168, thereby closing them. Any additional conduit orifices in the same plane as the conduits 164 and 168 will similarly be closed by the sealing element 162 in this position. In FIG. 14b, a connection is thus established between the cannula 172 and the conduit 166 through the connection point while other conduits are closed.

The sealing element can also be acted on by a fluid flowing through the conduits 166 and 170 so the element is deformed and seals other conduits.

Figure 15A:
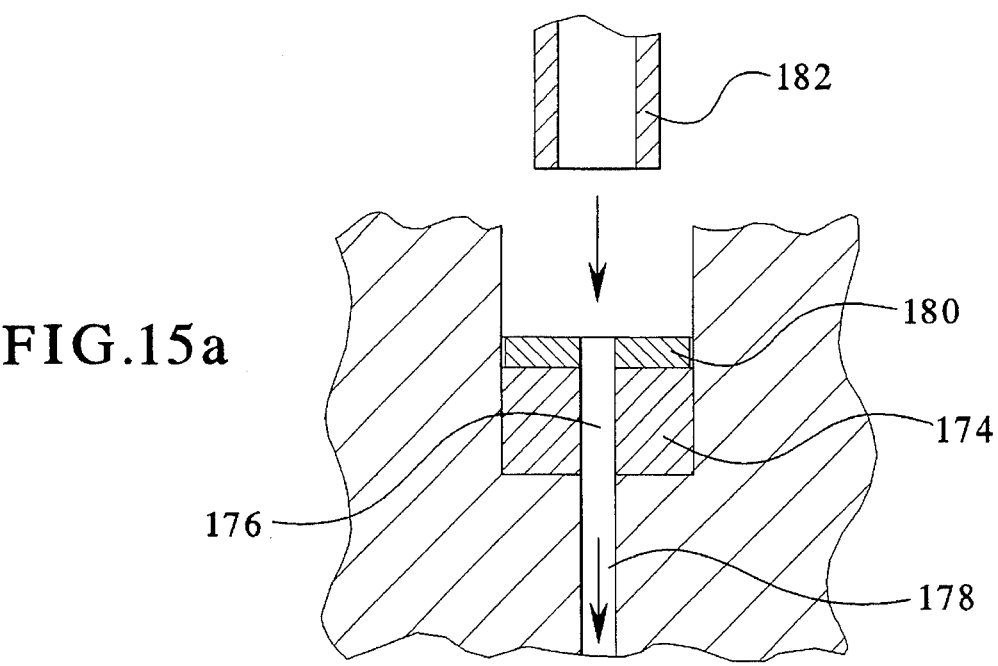
FIGS. 15a and 15b show a restriction device for a conduit for carrying a fluid.
Figure 15B:
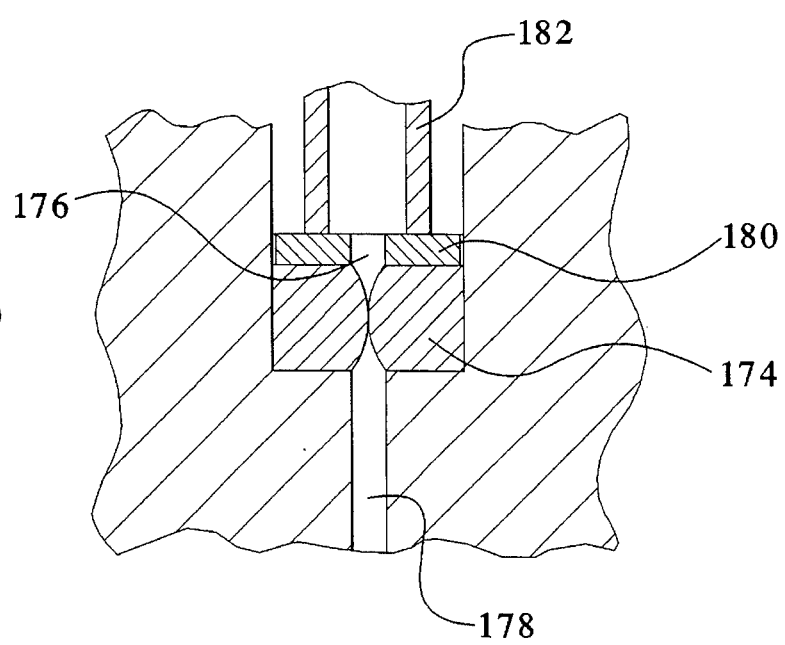

FIGS. 15a and 15b shows a restriction device containing a body 174 made of an elastic material arranged in a recess or in a stiff sleeve preventing radial expansion of the body 15. A channel 176, to which a conduit 178 is connected, runs through the body 174. A plate 180 made of a stiff material is arranged on the top of the body 174.

When the end of, e.g., an insertable tube 182, with a larger diameter than the diameter of the conduit 178, is pressed against the plate 180, the body 174 is axially compressed, the cross-section of the channel 176 thereby being reduced. Thus, a restriction, which depends on the magnitude of deformation of the body 174, arises in the channel 176. In FIG. 15a the body 174 is unaffected and in FIG. 15b it has been compressed, thereby completely closing the channel 176. Any desired size for a restriction can be achieved between these extreme positions.

The conduit 178 can alternatively be devised as a tube or a cannula which is inserted into the channel 176. An increased pressure and sealing against the tube or cannula is then obtained when the body 174 is compressed.

Although modifications and changes may be suggested by those skilled in the art, it is the intention of the inventors to embody within the patent warranted hereon all changes and modifications as reasonably and properly come within the scope of their contribution to the art.

We claim as our invention:

1. A coupling comprising:
   a plurality of conduits disposed in a connection piece to meet at a common interior connection point, said connection piece having an opening therein extending from an exterior of said connection piece into communication with said connection point; and
   a coupling element formed by a cannula having a longitudinal axis, said cannula being insertable into said opening and maneuverable in said connection piece by at least one of displacement along and rotation around said longitudinal axis to selectively define a flow path to at least one of said conduits while simultaneously blocking a flow path to at least one other of said conduits.

2. A coupling as claimed in claim 1 wherein said opening comprises at least a portion of one of said conduits.

3. A coupling as claimed in claim 2 further comprising a seal disposed between said cannula and said conduit into which said cannula is inserted.

4. A coupling as claimed in claim 3 wherein said seal comprises a ring seal.

5. A coupling as claimed in claim 3 wherein said seal comprises a septum seal.

6. A coupling as claimed in claim 1 further comprising means in said connection piece, engageable with said cannula, for fixing said cannula in at least one defined fixed position.

7. A coupling as claimed in claim 6 wherein said cannula has a flattened tip, and wherein said means for fixing comprises a slot adapted to receive said flattened tip, said slot being disposed in said connection piece at a side of said connection point opposite said opening.

8. A coupling as claimed in claim 1 further comprising means on said cannula for fixing an axial insertion position of said cannula along said longitudinal axis.

9. A coupling as claimed in claim I wherein said cannula comprises markings thereon identifying respective rotational positions of said cannula.

10. A coupling as claimed in claim 1 wherein said cannula has markings thereon identifying respective axial positions of said cannula along said longitudinal axis.

11. A coupling as claimed in claim 1 wherein said conduits are disposed in at least two levels in said connection piece, spaced from each other in a direction parallel to said longitudinal axis of said cannula, when inserted in said connection piece, and wherein said cannula comprises a hollow cylindrical body having a lateral wall with openings therein disposed so as to be co-planar with said levels of said conduits when said cannula is inserted into said connection piece, for selectively interconnecting respective conduits in said levels by at least one of displacement of said cannula along and rotation of said cannula around said longitudinal axis.

12. A coupling as claimed in claim 1 wherein said cannula comprises a tube having a fluid passage therein and having a tube wall with an opening therein disposed so as to communicate said passage with a conduit when said tube is inserted into said connection piece while blocking all others of said conduits.

13. A coupling as claimed in claim 12 wherein said tube wall has a plurality of openings therein, respectively alignable with individual ones of said conduits by at least one of displacement of said tube along and rotation of said tube around said longitudinal axis.

14. A coupling as claimed in claim 12 wherein said tube is insertable into one of said conduits, said one of said conduits having a conduit rim, and wherein said tube has a shoulder thereon which engages said conduit rim as said tube is inserted into said one of said conduits, for limiting the extent of insertion of said tube into said one of said conduits in the direction of said longitudinal axis.

15. A coupling as claimed in claim 12 wherein said tube has a closed tip.

16. A coupling as claimed in claim 12 wherein said tube has an open tip, communicating with said passage.

17. A coupling comprising:

a plurality of conduits disposed in a connection piece to meet at a common interior connection point, said connection piece having an opening therein extending from an exterior of said Connection piece into communication with said connection point;

an insertion element insertable into said opening; and a coupling element disposed at said common connection point and being maneuverable by said insertion element, when said insertion element is inserted into said opening, to selectively define a flow path to at least one of said conduits while simultaneously blocking a flow path to at least one other of said conduits.

18. A coupling as claimed in claim 17 wherein said coupling element comprises a cylinder contained in said connection piece so as to be rotatable around a cylinder axis by said insertion element, said cylinder having a first channel alignable by rotation of said cylinder with said opening to receive said insertion element, and at least one second channel alignable by rotation of said cylinder with a selected one of said conduits.

19. A coupling as claimed in claim 17 wherein said insertion element is insertable through said opening in an insertion direction, and wherein said coupling element comprises a slide contained in said connection piece and slidable in said connection piece in a plurality of directions perpendicular to said insertion direction, said slide having a first passage therein for receiving said insertion element and at least one second passage therein alignable with a selected one of said conduits when said slide is moved in said connection piece by said insertion element.

20. A coupling as claimed in claim 19 wherein said connection piece includes means for limiting sliding of said slide in said connection piece to cause said slide to remain in a position, after being moved by said insertion element, wherein said at least one second passage is aligned with said one of said conduits.

21. A coupling as claimed in claim 17 wherein said coupling element comprises a spring biased flap disposed at said connection point in front of one of said conduits, said flap being biased to normally open said one of said conduits and being movable by said insertion element, when inserted through said opening, to cover said one of said conduits.

22. A coupling as claimed in claim 17 wherein said coupling element comprises a compressible cylindrical tube disposed at said connection point and having an interior passage in registry with said opening, said compressible cylindrical tube being normally bowed inwardly to open said conduits and, upon insertion of said insertion element through said opening and through said passage in said compressible cylindrical tube, being forced against said conduits to block said conduits.

23. A coupling comprising:

a plurality of conduits disposed in a connection piece to meet at a common interior connection point, said connection piece having an opening therein extending from an exterior of said connection piece into communication with said connection point; and a compressible cylindrical tube disposed in said connection piece at said common connection point, said compressible cylindrical tube having a passage therein in registry with said opening, and said compressible cylindrical tube being normally bowed inwardly to open said conduits and being forced outwardly against said conduits to block said conduits upon the passage of fluid through said opening and through said passage.

* * * * *